(12) United States Patent
Kang et al.

(10) Patent No.: US 8,591,911 B2
(45) Date of Patent: Nov. 26, 2013

(54) XYLOGONE GANODERMOPHTHORA STRAIN WITH ANTIFUNGAL ACTIVITY, AND COMPOSITION INCLUDING SAME FOR PREVENTING PLANT DISEASES

(75) Inventors: Hyo Jung Kang, Chungbuk (KR); Ki Su Ahn, Chungbuk (KR); Chong Woo Han, Chungbuk (KR); Kyung Heon Jeong, Chungbuk (KR); See Jung Park, Ansan-si (KR); In Gyu Song, Cheongju-si (KR); Tae Yun, Cheongju-si (KR); Kyeong Beom Min, Cheongju-si (KR)

(73) Assignee: The Director of Chungcheongbuk-Do Agricultutal Research and Extension Services, Chungbuk (KR)

( * ) Notice: Subject to any disclaimer, the term of this patent is extended or adjusted under 35 U.S.C. 154(b) by 0 days.

(21) Appl. No.: 13/805,095

(22) PCT Filed: May 13, 2011

(86) PCT No.: PCT/KR2011/003529
§ 371 (c)(1),
(2), (4) Date: Feb. 7, 2013

(87) PCT Pub. No.: WO2012/067323
PCT Pub. Date: May 24, 2012

(65) Prior Publication Data
US 2013/0129774 A1 May 23, 2013

(30) Foreign Application Priority Data
Nov. 18, 2010 (KR) .................. 10-2010-0114971

(51) Int. Cl.
*A01N 63/04* (2006.01)
*A61K 36/06* (2006.01)
*C12N 1/00* (2006.01)

(52) U.S. Cl.
USPC .................. 424/195.16; 435/254.1

(58) Field of Classification Search
None
See application file for complete search history.

(56) References Cited

U.S. PATENT DOCUMENTS 5,123,203 A * 6/1992 Hiromoto ................ 47/1.1

FOREIGN PATENT DOCUMENTS

| JP | 2001-247566 A | | 9/2001 |
| KR | 98069226 | * | 10/1998 |
| KR | 10-0315098 B1 | | 11/2001 |
| KR | 10-2006-0012393 A | | 2/2006 |

OTHER PUBLICATIONS

Lee et al. Korean J. Mycology. 1996. vol. 24, No. 4, pp. 246-254.*
International Search Report for PCT/KR2011/003529, Feb. 28, 2012.
Kang, Hyo Jung et al., "Xylogone ganodennophthora sp. nov., an ascomycetous pathogen causing yellow rot on cultivated mushroom *Ganoderma lucidm* in Korea", Mycologia, Oct. 2010, vol. 102, No. 5, pp. 1167-1184, see p. 1179.

* cited by examiner

*Primary Examiner* — Chris R Tate
*Assistant Examiner* — Douglas F White
(74) *Attorney, Agent, or Firm* — The PL Law Group, PLLC

(57) ABSTRACT

A novel ascomycetous *Xylogone ganodermophthora* strain has antifungal activity. A composition includes the strain as an active ingredient for preventing plant diseases. A method for producing the composition includes culturing the strain, and a method for preventing plant diseases includes using the strain. The strain suppresses the growth of pathogenic fungi, including *Phytophthora capsici*, in plants. Therefore, the composition containing the strain, or a culture or extract thereof, as an active ingredient for preventing plant diseases has excellent antifungal activity and can thus be used as an environmentally friendly and pollution-free pesticide.

8 Claims, 6 Drawing Sheets

(a)

(b)

(c)

(d)

Figure 1:
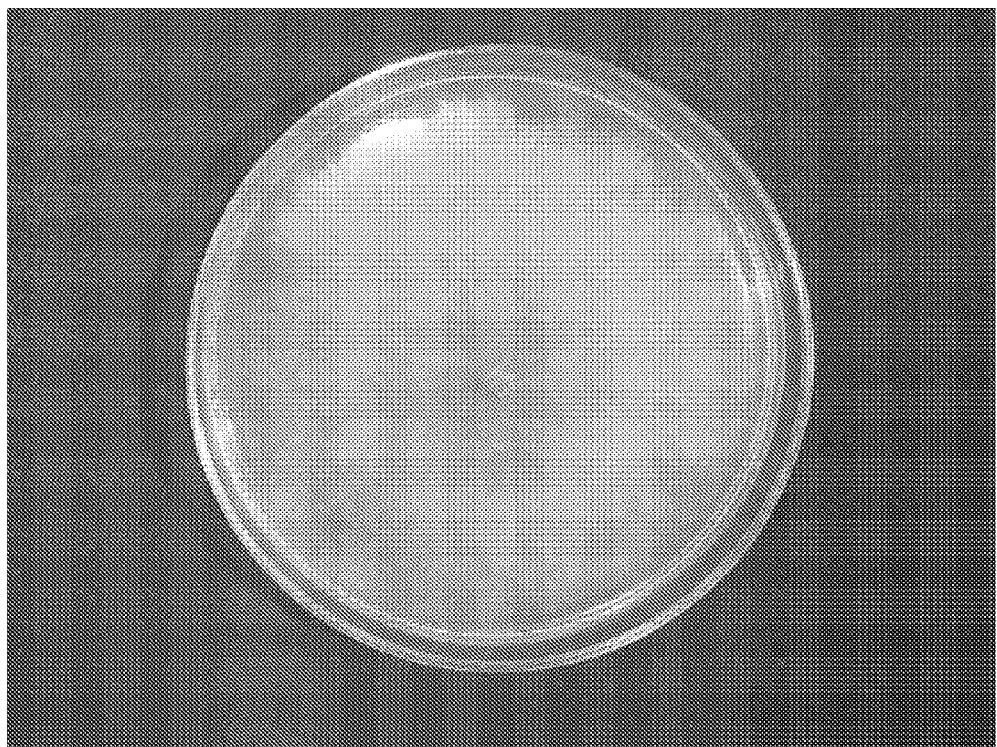

SEQUENCE LISTING

<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<223> OTHER INFORMATION: ITS primer (ITS1)

<400> SEQUENCE: 1
tccgtaggtg aacctgcgg                                              19

<210> SEQ ID NO 2
<211> LENGTH: 20
<212> TYPE: DNA
<213> ORGANISM: Artificial Sequence
<220> FEATURE:
<223> OTHER INFORMATION: ITS primer (ITS4)

<400> SEQUENCE: 2
tcctccgctt attgatatgc                                             20

<210> SEQ ID NO 3
<211> LENGTH: 539
<212> TYPE: DNA
<213> ORGANISM: Xylogone ganodermophthora H55

<400> SEQUENCE: 3
agggatcatt accgagttca tgccccacag cggggtagat ctcccaccct tgtgtattta      60
tacctgtgtt gctttggcag gccgctgggc tgcggtctgg ccaccggctt cttcgaagct     120
ggtgcgtgcc tgccagaggc cccccaaact cttgtttgtc tagtgttgtc tgagtatcat     180
accaatcgtt aaaactttca acaacggatc tcttggttcg ggcatcgatg aagaacgcag     240
cgaaatgcga taagtaatgc gaattgcaga attcagtgaa tcatcgaatc tttgaacgca     300
cattgcgccc cttggtattc cgaggggcat gcctgttcga gcgtcatttc aaccctcaa     360 gctctgcttg gtattgggcc tcgccatcgc ggcgggcctt aaaatcagtg gcggtgccgt     420
ctcggctcca agcgtagtag catcatctcg ctctggagac ccggcggttg ctggccagat     480 aaccccaat tttttctgtg gttgacctcg gatcaggtag ggatacccgc tgaacttaa     539

<210> SEQ ID NO 4
<211> LENGTH: 1340
<212> TYPE: DNA
<213> ORGANISM: Xylogone ganodermophthora H55
<220> FEATURE:
<221> NAME/KEY: misc_feature
<222> LOCATION: (1054)..(1153)
<223> OTHER INFORMATION: n is a, c, g, or t

<400> SEQUENCE: 4
ttaacacagg atgtctacaa gtacttacag cgatgtgttg aaaataaccg tgagttcaat      60
ttgacacttg gagtaaaatc cacaacattg accaacggtc ttaaatactc attggctact     120
ggaaattggg gagatcaaaa gaaggctgca agctcgacag ctggtgtgtc tcaggtgctc     180
aacagatata catttgcctc tacgctttct catttgcggc gaaccaatac acctattggt     240
cgtgatggaa agattgctaa acctcggcag cttcataaca ctcattgggg tctggtttgt     300
cccgccgaga ctccagaagg tcaagcttgt ggtctcgtca agaatctcgc tctcatgtgt     360
tatgttactg tcggtactcc tagtgacccc atcgttgagt tcatgattca acgaaatatg     420

```
gaagtgctcg aggaatacga cccagtcaga tcaccaaata tgaccaaggt cttcgtcaat    480
ggtgtttggg taggagttca tcgcgaaccc gctcatctcg ttagcaccgt gcaacatctc    540
cgacgttctc atttgatctc acatgaagta tctctaatta gagatattcg tgaccgggaa    600
ttcaagatct tcacagatgc gggcagagtc tgcagaccat tgttcgttat tgataatgat    660
gttgatagcg cgaacaaagg taacttggtg ctcaacaaag accatattcg aaggctagag    720
gaagatcaaa caatgcctgc aaacatggat atggaacagc gaaaggaagc aggttatttc    780
ggtttccaag gtttaatcaa tgagggtgtg gttgaatatg tagacgccga agaagaggaa    840
acgattatga tagtgatgac tccagaagat ctagatattt ctcgacaact acaagccgga    900
tatcagatca gacctgatga gagtggagat atgaacaaac gtgttaaggc tccaatgaac    960
ccaacggcgc atatctggac gcattgtgaa atccacccaa gtatgattct gggtatttgt   1020
gccagtatca ttccattccc ggatcataat cagnnnnnnn nnnnnnnnnn nnnnnnnnnn   1080
nnnnnnnnnn nnnnnnnnnn nnnnnnnnnn nnnnnnnnnn nnnnnnnnnn nnnnnnnnnn   1140
nnnnnnnnnn nnnggagtgt tccttactaa tttcgatcaa cgtatggata ccatggccaa   1200
tatcttgtac tatcctcaga aaccacttgc taccacacgt tctatggaat tcttgaagtt   1260
cagagagttg ccagcagggc agaatgcaat cgtcgctatc gcatgttact ccggttacaa   1320
tcaagaagat tccgttatta                                               1340
```

<210> SEQ ID NO 5
<211> LENGTH: 2267
<212> TYPE: DNA
<213> ORGANISM: Xylogone ganodermophthora H55
<220> FEATURE:
<221> NAME/KEY: misc_feature
<222> LOCATION: (3)..(3)
<223> OTHER INFORMATION: n is a, c, g, or t

<400> SEQUENCE: 5

```
agntctgtct cagattagcc atgcatgtct aagtataagc aactatactg tgaaactgcg     60
aatggctcat taaatcagtt atcgtttatt tgatagtacc ttactacttg gataaccgtg    120
gtaattctag agctaataca tgctaaaaac ctcgacttcg gaaggggtgt atttattaga    180
taaaaaacca atgcccttkcg gggctccttt ggtkattcaa waataactwa acgaatcgca    240
tggccttgtg ccggcgatgg ttcattcaaa tttctgccct atcaactttc gatggtagga    300
tagtggccta ccatggtttc aacgggtaac ggggaattag ggttctattc cggagaagga    360
gcstgagaca cggctcctac atccaaggaa ggcagcaggc gcgcaaatta cccaatcccg    420
acacggggag gtagtgacaa taaatactga tacagggctc ttttgggtct tgtaattgga    480
atgagtacaa tttaaatccc ttaacgagga acaattggag ggcaagtctg gtgccagcag    540
ccgcggtaat tccagctcca atagcgtata ttaaagttgt tgcagttaaa aagctcgtag    600
ttgaaccttg ggcctggctg gccggtccgc ctcaccgcgt gcactggtcc ggccgggcct    660
ttccttctgg ggagccgcat gcccttcact gggtgtgtcg gggaaccagg acttttactt    720
tgaaaaaatt agagtgttca aagcaggcct atgctcgaat acattagcat ggaataatag    780
aataggacgt gtggttctat tttgttggtt tctaggaccg ccgtaatgat taatagggat    840
agtcgggggc atcagtattc aattgtcaga gtgaaattc ttggatttat tgaagactaa    900
ctactgcgaa agcatttgcc aaggatgttt tcattaatca gtgaacgaaa gttaggggat    960
cgaagacgat cagataccgt cgtagtctta accataaact atgccgacta gggatcgggc   1020
gatgttactt ttttgactcg ctcggcacct tacgagaaat caaagtcttt gggttctggg   1080
```

-continued

```
gggagtatgg tcgcaaggct gaaacttaaa gaaattgacg gaagggcacc acaatggagt    1140
ggagcctgcg gcttaatttg actcaacacg gggaaactca ccaggtccag acacaataag    1200
gattgacaga ttgagatgcc tctttcttga ttttgtgggt ggtggtgcat ggccgttctt    1260
agttggtgga gtgatttgtc tgcttaattg cgataacgaa cgagaccwta acctactaaa    1320
tagccaggct agctttggct ggtcgccggc ttcttagagg gactatcggc tcaagccgat    1380
ggaagtttga ggcaataaca ggttaacttc acaggcctgt aaaagcaggt ctcagacttt    1440
cagtggggaa tgctggataa ctgctagtac accatctaat cgctgtgggg cgagtgcccc    1500
cattatgagg cagcgaccgt tcaggtgatg ggtgcgagac aacctggtac aggggacgcc    1560
agtccgtcac tcggtgatgg gcgggtcaat cctgtggcga gataggtaac gactatccgt    1620
cgcaacgcac gctaargtgt cggtctactg gatatccggt aggcttaarg tacgtgctat    1680
cccccgtgta agcgggcctc gagaaatagg actcataagc cgaagtctcg agggatgcag    1740
atttaggagt tctgtgaaat cactgatctg cattggggtt gttacttttg agattttca    1800 gataaytgga tttcattggg aatcacgcga cagcagtcgc ggtgaactcg atttctctca    1860
gaatacatgg tggggtgcag gtgcattcat gcagccgcaa gagaatccca aacaatgaat    1920
ccaattcgaa gaagttatca aaggtgacaa tgaaatgctg tgatgccctt agatgttctg    1980
ggccgcacgc gcgctacact gacagagcca acgagttcat caccttggtc gaaaggcctg    2040
ggtaatcttg ttaaactctg tcgtgctggg gatagagcat tgcaattatt gctcttcaac    2100
gaggaattcc tagtaagcgc aagtcatcag cttgcgttga atacgtccct gccctttgta    2160
cacaccgccc gtcgctacta ccgattgaat ggctcagtga ggctttcgga ctggcctagg    2220
aagagtggca acactcatcc agggccggaa agttacaaat cttttcc                  2267
```

XYLOGONE GANODERMOPHTHORA STRAIN WITH ANTIFUNGAL ACTIVITY, AND COMPOSITION INCLUDING SAME FOR PREVENTING PLANT DISEASES

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2011/003529, filed May 13, 2011, which claims priority to Korean Patent Application No. 10-2010-0114971, filed Nov. 18, 2010, entire contents of which are incorporated herein by reference.

BACKGROUND OF THE INVENTION

1. Field of the Invention

The present invention relates to a novel strain of *Xylogone ganodermophthora* having antifungal activity against various pathogenic fungi. The above *Xylogone ganodermophthora* is a novel species identified by the present inventors. The present invention also relates to a composition for controlling plant diseases, particularly *Phytophthora capsici*, which comprises the above strain, a preparation method thereof and a method for controlling plant diseases using the same.

2. Description of the Prior Art

The control of plant diseases have been mainly based on the wide use of noxious chemicals (agricultural chemicals). Control methods based on such organic synthetic agricultural chemicals cause problems of residual toxicity in crops and soil, because not only target plants and products of the plants, but also soil are frequently treated with noxious chemical substances. It is known that, among these chemicals, many compounds are toxic to microorganisms and animals in addition to target organisms and can also be harmful to humans. Thus, significant portions of recent studies on the control of plant diseases aims to find environment-friendly methods for controlling plant diseases, and one thereof is the development of biological agricultural chemicals based on biological resources antagonist against plant pathogenic microorganisms. As used herein, the term "antagonist microorganisms" refers to microorganisms that inhibit the growth of other kinds of microorganisms when they are cultured with the other microorganisms. The antagonist microorganisms are known to have parasitic, phagocytic and antibiotic activities, etc. Examples of antagonist microorganisms having antifungal activity against pathogenic fungi include *Bacillus subtilis* var *amyloliquefaciens* KL1114 (accession No: KCTC 8913P) disclosed in Korean Patent Registration No. 10-0325634, *Streptomyces* spp. WYE 20 (KCTC 8768P) and WYE 324 (KCTC 8769P) disclosed in Korean Patent Registration No. 10-0197077, and improved *Promicromonospora* sp. KH-28 KCTC8946P) disclosed in Korean Patent Registration No. 10-0333039.

Under such circumstances, the present inventors isolated and identified *Xylogone sphaerospora* causing Norang diseases in *Ganoderma lucidum*. During these isolation and identification procedures, the present inventors have discovered a novel strain showing antifungal activity against various pathogenic fungi, and particularly, have found that an organic solvent extract of a culture of this strain has an antifungal activity against *Phytophthora capsici*, thereby completing the present invention.

*Phytophthora capsici* has been classified as belonging to the class Oomycetes of the subdivision Mastigomycotina, but has recently been classified as plant pathogenic fungi belonging to the Chromista group. *Phytophthora capsici* forms zoospores and spreads from diseased plants to healthy plants through irrigation water and the like. *Phytophthora* blight that occurred at roots progresses along stems, but in fields in which *Phytophthora* blight severely occurred, infection of pepper fruits or leaves sometimes occurs directly from soil. In the winter season, *Phytophthora capsici* forms macrospora, passes the winter and acts as a primary infectious source in the next year. *Phytophthora* blight occurs mainly in repeated-cultivation farms and spreads rapidly in the rainy season to cause wide economic damage. In addition, it also occurs on seedlings, and due to recent climate warming, it also occurs within one month after planting. In farms which are damaged by the habitual occurrence of *Phytophthora* blight, the control of *Phytophthora* blight is performed by methods, including crop rotation, chemical control based on organic synthetic agricultural chemicals, or cultivation of *Phytophthora* blight resistant varieties. As a cultural method for controlling *Phytophthora* blight, crop rotation is performed, but when an external infectious source is introduced, great damage will be caused if chemical control based on synthetic agricultural chemicals is not performed timely. In farms in which *Phytophthora* blight habitually occurs but crop rotation cannot be performed, the use of *Phytophthora* blight-resistant varieties can be an effective control method, but the seeds of the varieties are costly, and when a resistant strain appears, it can cause great damage. Thus, the control of *Phytophthora* blight by synthetic agricultural chemicals is actually difficult to exclude. In current farms, the control of *Phytophthora* blight by synthetic agricultural chemicals is generally performed, but damage such as the disturbance of the agroecosystem caused by the improper use of synthetic agricultural chemicals is increasing. Accordingly, as a part of an environment-friendly agricultural policy for reducing the use of synthetic agricultural chemicals, biological agricultural chemicals, including microbial agricultural chemicals and biochemical chemicals, are emerging as an alternative to the synthetic agricultural chemicals.

SUMMARY OF THE INVENTION

It is an aspect of the present invention to provide *Xylogone ganodermophthora*, a novel ascomycetous species having antifungal activity against pathogenic fungi.

Another aspect of the present invention is to provide a composition for controlling a plant disease, which comprises the above strain or a culture or extract of the strain, a preparation method thereof and a method for controlling a plant disease using the same.

To achieve the above aspects, an embodiment of the present invention provides *Xylogone ganodermophthora*, a novel ascomycetous species. The above strain is, for example, *Xylogone ganodermophthora* H55 (accession number: KACC 93082P; deposited on Oct. 27, 2009), but is not limited thereto. The *Xylogone ganodermophthora* strain has antifungal activity. The *Xylogone ganodermophthora* strain has antifungal activity against an animal pathogenic fungus or a plant pathogenic fungus. For example, it has antifungal activity against a plant pathogenic fungus.

The kind of plant pathogenic fungus against which the strain of the present invention can exhibit antifungal activity is not limited and includes all pathogenic fungi capable of infecting plants. The plant pathogenic fungus may be *Phytophthora capsici, Sphaerotheca fusca, Colletotrichum acutatum, Rhizoctonia solani, Fusarium moniliforme, Sclerotinia cepivorum, Sclerotinia sclerotiorum* or *Didymella*

*bryoniae*. For example, the plant pathogenic fungus is *Phytophthora capsici* or *Sphaerotheca fusca*.

The kind of plant on which the present invention can exhibit antifungal activity is not limited and includes all plants which can be infected with a plant pathogenic fungus. The plant may be a *Cucurbitaceae* plant, for example, a *Lagenaria, Luffa, Cucurbita* or *Cucumis* plant, and particularly a gourd, a cucumber, a pumpkin, an oriental melon or a melon.

In a second aspect, the present invention provides the above strain or a pure culture thereof, and a microbial formulation for controlling a plant disease, which comprises the above strain or pure culture as an active ingredient. The culture may be any culture produced from a medium under conditions in which the strain can normally grow, and is not limited to a specific culture condition. The microbial formulation may contain any additive which is generally used for formulation or storage.

The kind of plant disease against which the present invention exhibits antifungal activity is not limited and includes all plant diseases caused by the infection of plants with plant pathogenic fungi. The plant disease may be a *Phytophthora* blight, *Sphaerotheca fusca, Colletotrichum acutatum, Rhizoctonia solani, Fusarium moniliforme, Sclerotinia cepivorum, Sclerotinia sclerotiorum* or *Didymella bryoniae* disease, and, for example, a *Phytophthora capsici* or *Sphaerotheca fusca* disease.

In a third embodiment, the present invention provides a culture extract of the above strain, and a composition for controlling a plant disease, which comprises the extract as an active ingredient. A solvent which can be used in the extraction of the strain may be any solvent known in the art. For example, the strain may be extracted using water, $C_{1-4}$ anhydrous or hydrated lower alcohol (methanol, ethanol, propanol, butanol, n-propanol, iso-propanol, n-butanol, etc.), a mixed solvent of the lower alcohol and water, acetone, ethyl acetate, chloroform, 1,3-butyleneglycol, hexane, or diethyl ether. For example, the strain culture may be extracted with methanol or ethyl acetate after being dissolved in methanol.

The kind of plant disease which may be controlled by the present invention is not limited and includes all plant diseases to be controlled by preventing or controlling the infection of plants with plant pathogenic fungi. The plant disease may be a *Phytophthora capsici, Sphaerotheca fusca, Colletotrichum acutatum, Rhizoctonia solani, Fusarium moniliforme, Sclerotinia cepivorum, Sclerotinia sclerotiorum* or *Didymella bryoniae* disease, and for example, a *Phytophthora capsici* or *Sphaerotheca fusca* disease.

In a fourth aspect, the present invention provides a method for preparing a composition for controlling a plant disease, the method comprising the steps of: culturing *Xylogone ganodermophthora*; dissolving the cultured *Xylogone ganodermophthora* in a solvent, followed by extraction; and formulating the extract. A solvent which can be used in the extraction of the strain may be any solvent known in the art. According to an embodiment of the present invention, the strain may be extracted using water, $C_{1-4}$ anhydrous or hydrated lower alcohol (methanol, ethanol, propanol, butanol, n-propanol, iso-propanol, n-butanol, etc.), a mixed solvent of the lower alcohol and water, acetone, ethyl acetate, chloroform, 1,3-butyleneglycol, hexane, or diethyl ether. For example, the extracting step is performed by extracting the cultured strain with methanol or ethyl acetate and concentrating the extract under reduced pressure.

The kind of plant disease which may be controlled by the present invention is not limited and includes all plant diseases to be controlled by preventing or controlling the infection of plants with plant pathogenic fungi. The plant disease may be a *Phytophthora capsici, Sphaerotheca fusca, Colletotrichum acutatum, Rhizoctonia solani, Fusarium moniliforme, Sclerotinia cepivorum, Sclerotinia sclerotiorum* or *Didymella bryoniae* disease, and for example, a *Phytophthora capsici* or *Sphaerotheca fusca* disease.

In a fifth aspect, the present invention provides a method for controlling a plant disease, which comprises spraying onto a host plant an effective amount of the composition for controlling a plant disease, prepared by the above preparation method.

BRIEF DESCRIPTION OF THE DRAWINGS

FIG. 1 is a photograph of a *Xylogone ganodermophthora* H55 strain cultured on a potato dextrose agar medium at 26° C. for 4 days.

FIG. 2 is a set of photographs showing the results obtained by culturing a *Xylogone ganodermophthora* strain and three other strains, known to be similar to the *Xylogone ganodermophthora* strain, under the same conditions. In FIG. 2, (a): *Xylogone ganodermophthora* H55, (b): *Xylogone sphaerospora*, (c): *Arthrographis cuboidea* UAMH 676, and (d): *Sporendonema purascens* UAMH 1497.

FIG. 3 shows the most parsimonious tree obtained in parsimony analysis using the nucleotide sequence of the ITS region. The values indicated on the branches of the parsimonious tree are bootstrap support values of 50 or more in bootstrap analysis (100 replications). The branch length is in proportion to the degree of nucleotide substitution. In FIG. 3, H55 indicates *Xylogone ganondermophthora* H55; UAMH 1497 indicates *Sporendonema purpurascens* UAMH 1497; KACC 41228 indicates *Scytalidum lignicola* KACC 41228; ATCC 34392 indicates *Xylogone sphaerospora* ATCC34392; and UAMH 676 indicates *Arthrographis cuboidea* UAMH 676.

FIG. 4 shows the most parsimonious tree obtained in parsimony analysis using the nucleotide sequence of RPB2 gene. No bootstrap support value was indicated on the branches of the parsimonious tree, because a bootstrap support value of 50 or more was not present in bootstrap analysis (100 replications). The branch length in the parsimonious tree is in proportion to the degree of nucleotide substitution. In FIG. 4, H55 indicates *Xylogone ganondermophthora* H55; UAMH 1497 indicates *Sporendonema purpurascens* UAMH 1497; KACC 41228 indicates *Scytalidum lignicola* KACC 41228; ATCC34392 indicates *Xylogone sphaerospora* ATCC34392; and UAMH 676 indicates *Arthrographis cuboidea*) UAMH 676.

FIG. 5 shows the antagonist properties of a methanol extract of the inventive *Xylogone ganondermophthora* H55 strain against *Phytophthora capsici*. In FIG. 5, upper: 0 ppm disc, lower: 1,000 ppm disc, left: 100 ppm disc, and right: 10,000 ppm disc.

FIG. 6 shows the antagonist properties of an ethylacetate extract of the inventive *Xylogone ganondermophthora* H55 strain against *Phytophthora capsici*. In FIG. 6, upper: 0 ppm disc, lower: 1,000 ppm disc, left: 100 ppm disc, and right: 10,000 ppm disc.

DETAILED DESCRIPTION OF THE INVENTION

An embodiment of the present invention provides *Xylogone ganodermophthora*, a novel ascomycetous species. The above strain is, for example, *Xylogone ganodermophthora* H55 (accession number: KACC 93082P; deposited on Oct. 27, 2009), but is not limited thereto. The *Xylogone gano-*

*dermophthora* strain has antifungal activity. The *Xylogone ganodermophthora* strain has antifungal activity against an animal pathogenic fungus or a plant pathogenic fungus. For example, it has antifungal activity against a plant pathogenic fungus.

The kind of plant pathogenic fungus against which the strain of the present invention can exhibit antifungal activity is not limited and includes all pathogenic fungi capable of infecting plants. The plant pathogenic fungus may be *Phytophthora capsici, Sphaerotheca fusca, Colletotrichum acutatum, Rhizoctonia solani, Fusarium moniliforme, Sclerotinia cepivorum, Sclerotinia sclerotiorum* or *Didymella bryoniae*. For example, the plant pathogenic fungus is *Phytophthora capsici* or *Sphaerotheca fusca*.

The kind of plant on which the present invention can exhibit antifungal activity is not limited and includes all plants which can be infected with a plant pathogenic fungus. The plant may be a *Cucurbitaceae* plant, for example, a *Lagenaria, Luffa, Cucurbita* or *Cucumis* plant, and particularly a gourd, a cucumber, a pumpkin, an oriental melon or a melon.

In a second aspect, the present invention provides the above strain or a pure culture thereof, and a microbial formulation for controlling a plant disease, which comprises the above strain or pure culture as an active ingredient. The culture may be any culture produced from a medium under conditions in which the strain can normally grow, and is not limited to a specific culture condition. The microbial formulation may contain any additive which is generally used for formulation or storage.

The kind of plant disease against which the present invention exhibits antifungal activity is not limited and includes all plant diseases caused by the infection of plants with plant pathogenic fungi. The plant disease may be a *Phytophthora* blight, *Sphaerotheca fusca, Colletotrichum acutatum, Rhizoctonia solani, Fusarium moniliforme, Sclerotinia cepivorum, Sclerotinia sclerotiorum* or *Didymella bryoniae* disease, and, for example, a *Phytophthora capsici* or *Sphaerotheca fusca* disease.

In a third embodiment, the present invention provides a culture extract of the above strain, and a composition for controlling a plant disease, which comprises the extract as an active ingredient. A solvent which can be used in the extraction of the strain may be any solvent known in the art. For example, the strain may be extracted using water, $C_{1-4}$ anhydrous or hydrated lower alcohol (methanol, ethanol, propanol, butanol, n-propanol, iso-propanol, n-butanol, etc.), a mixed solvent of the lower alcohol and water, acetone, ethyl acetate, chloroform, 1,3-butyleneglycol, hexane, or diethyl ether. For example, the strain culture may be extracted with methanol or ethyl acetate after being dissolved in methanol.

The kind of plant disease which may be controlled by the present invention is not limited and includes all plant diseases to be controlled by preventing or controlling the infection of plants with plant pathogenic fungi. The plant disease may be a *Phytophthora capsici, Sphaerotheca fusca, Colletotrichum acutatum, Rhizoctonia solani, Fusarium moniliforme, Sclerotinia cepivorum, Sclerotinia sclerotiorum* or *Didymella bryoniae* disease, and for example, a *Phytophthora capsici* or *Sphaerotheca fusca* disease.

In a fourth aspect, the present invention provides a method for preparing a composition for controlling a plant disease, the method comprising the steps of: culturing *Xylogone ganodermophthora*; dissolving the cultured *Xylogone ganodermophthora* in a solvent, followed by extraction; and formulating the extract. A solvent which can be used in the extraction of the strain may be any solvent known in the art.

According to an embodiment of the present invention, the strain may be extracted using water, $C_{1-4}$ anhydrous or hydrated lower alcohol (methanol, ethanol, propanol, butanol, n-propanol, iso-propanol, n-butanol, etc.), a mixed solvent of the lower alcohol and water, acetone, ethyl acetate, chloroform, 1,3-butyleneglycol, hexane, or diethyl ether. For example, the extracting step is performed by extracting the cultured strain with methanol or ethyl acetate and concentrating the extract under reduced pressure.

The kind of plant disease which may be controlled by the present invention is not limited and includes all plant diseases to be controlled by preventing or controlling the infection of plants with plant pathogenic fungi. The plant disease may be a *Phytophthora capsici, Sphaerotheca fusca, Colletotrichum acutatum, Rhizoctonia solani, Fusarium moniliforme, Sclerotinia cepivorum, Sclerotinia sclerotiorum* or *Didymella bryoniae* disease, and for example, a *Phytophthora capsici* or *Sphaerotheca fusca* disease.

In a fifth aspect, the present invention provides a method for controlling a plant disease, which comprises spraying onto a host plant an effective amount of the composition for controlling a plant disease, prepared by the above preparation method.

Hereinafter, the present invention will be descried in further detail with reference to examples. It will be obvious to those skilled in the art that these examples are for illustrative purposes and are not intended to limit the scope of the present invention.

EXAMPLE 1

Isolation and Identification of Xylogone ganodermophthora (1) Isolation of Strain In 2001, *Ganoderma lucidum* residue and the oak tissue of cultivation woods were collected from cultivation soils throughout Korea. The collected sample was observed under a steroscopic microscope while black ascocarps were separated therefrom, and the size and shape of the black ascocarps were observed under an optical microscope. Such ascocarps were immersed in a 2% NaCl solution and subjected to surface sterilization for 1-2 minutes, and then plated on a potato dextrose agar medium to induce mycelial growth. Monospores were separated from the growing mycelia and stored at −70° C. for a long period of time.

The above strain had characteristics different from those of known ascomycetes with respect to the results of analysis of morphological characteristics, the nucleotide sequence of ITS, the nucleotide sequence of 18S rDNA gene and the nucleotide sequence of RPB2 gene, as described below. Thus, the above strain was named "*Xylogone ganodermophthora*" as a novel strain, and *Xylogone ganodermophthora* H55 was deposited with the Korean Agricultural Culture Collection, the National Academy of Agricultural Science, on Oct. 27, 2009 under the accession number KACC 93082P.

(2) Morphological Characteristics

The strain was cultured on the potato dextrose agar medium, and as a result, the morphologies of colonies on the culture medium were substantially the same, and thus the morphological difference between these colonies could not be observed. From such strains, 10 regional typical strains were selected and the various morphological and cultural characteristics thereof were examined.

When the H55 strain was cultured on the potato dextrose agar medium at 26° C., it secreted a yellow pigment onto the medium after 4 days, and the medium started to be yellowed.

After 2 weeks, a large amount of arhrospores were formed, and thus the medium had pink (FIG. 1). The shape of the arthrospores was cylindrical and the length thereof was greater than the width, and the arthrospores had a size of about 1.5×5 to 1.5×3 μm.

Figure 2:
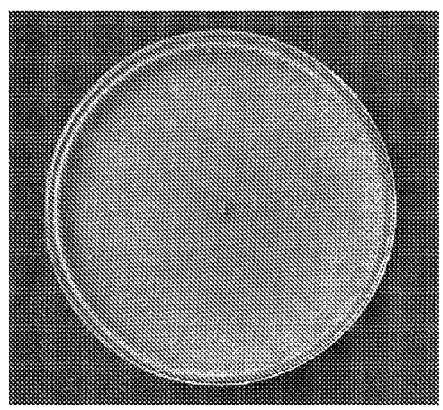
Figure 2:
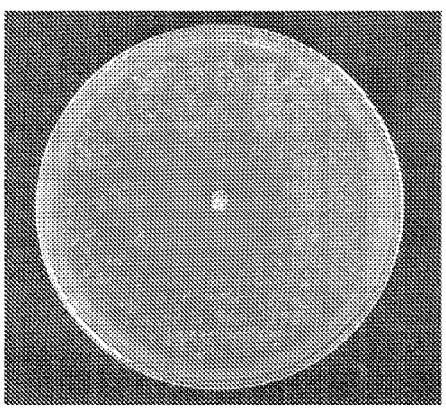
Figure 2:
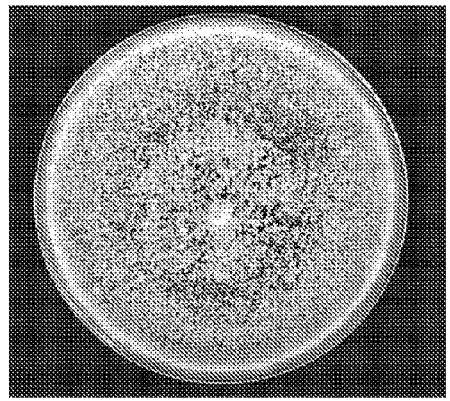
Figure 2:
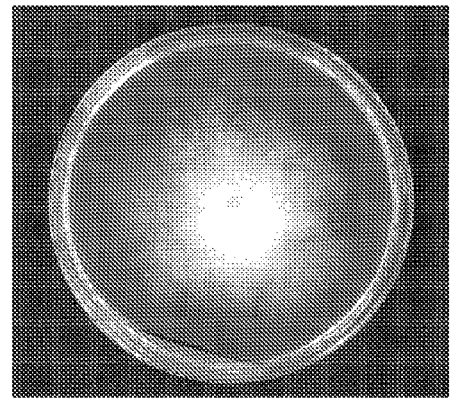

When the strain was cultured for about 4 weeks, ascocarps were formed while the back side of the plate medium changed from brown to dark brown, and the surface of the cultured strain changed to light greenish yellow. The teleomorph of the H55 strain was morphologically similar to the ascomycetous fungus *Xylogone spaherospor*, but the size of the ascocarps and the shape of the ascospores in the strain did differ from those of *Xylogone spaherospor*, and the morphological characteristics thereof on the culture medium did clearly differ. Specifically, the ascospores of the H55 strain were globose or subglobose, and the surface thereof was smooth, transparent and glittering. The size of the ascospores was 3.3-4.3×3-4 μm. The arthrospores of the H55 strain did clearly differ from those of *Arthrographis cuboidea*, although the shape thereof was similar to that of the arthrospores of *Arthrographis cuboidea*. In addition, the shape of colonies on the culture medium did significantly differ from that of colonies of *Arthrographis cuboidea* (FIG. 2).

(3) Analysis of Nucleotide Sequence of ITS Region

For the genetic analysis and identification of the H55 strain, the nucleotide sequence of the ITS region was determined according to the method described in the literature (White T J, Bruns T, Lee S, Taylor J, 1990, Amplification and direct sequencing of fungal ribosomal RNA genes for phylogenetics. In: Innis A M, Gelfand D H, Sninsky J J, White T J, (eds), PCR Protocols: A guide to methods and application. Academic Press, San Diego, pp. 315-322).

The H55 strain cultured in PD broth (Potato Dextrose Broth) for 7 days, and then the mycelium was collected and freeze-dried, and DNA was extracted therefrom using liquid nitrogen. The extracted DNA was amplified by PCR (polymerase chain reaction) in 50 μl of the following reaction mix using universal ITS primers, that is, ITS1 (5'-TCCGTAGGT-GAACCTGCGG-3', SEQ ID NO: 1) and ITS4 (5'-TCCTC-CGCTTATTGATATGC-3', SEQ ID NO: 2).

Reaction mix: 1 μl of ITS1 primer (10 pmoles/μl), 1 μl of ITS 4 primer (10 pmoles/μl), 4 μl of dNTP mixtures, 5 μl of rTaq PCR buffer (5% deoxynucleotide triphosphates, 40% 25 mM MgCl$_2$, 50% 10×PCR buffer, 5% water), 37.7 μl of water, 0.25 μl of polymerase (5 U/μl) and 1 μl of template DNA.

Moreover, the PCR amplification was performed under the following conditions: predenaturation at 94° C. for 2 min; and then 30 cycles of 1 min at 94° C., 1 min at 50° C. and 2 min at 72° C.; followed by final extension at 72° C. for 10 min.

The PCR product was purified by a GenClean Turbo DNA purification kit, and then sequenced by an automatic sequencer. The determined sequence was compared with the GenBank database using BLASTN and, as a result, it showed a homology of 90% with *Scytalidum lignicola*. The ITS nucleotide sequence of the *Xylogone ganodermophthora* H55 strain is represented by SEQ ID NO: 3.

Figure 3:
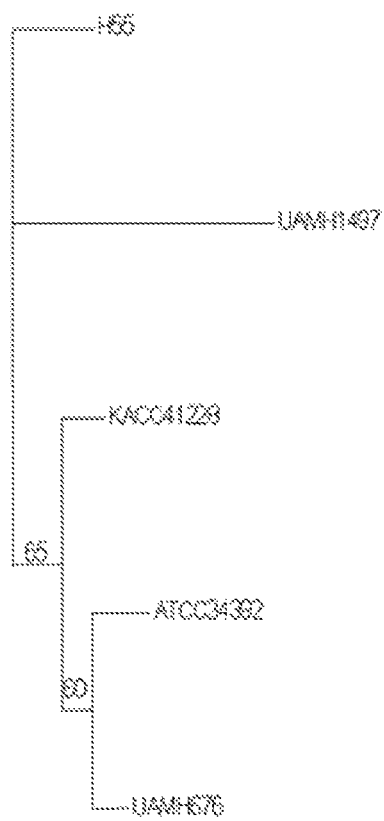

The ITS nucleotide sequence was automatically aligned by the method of Clustal W using the Meg Alignment program, and then the most parsimonious tree (MP tree) was obtained using the PAUP 4.0 beta b version statistical program. The optimality criterion was set to maximum parsimony. The nucleotide sequence of a *Sporendonema purpurascens* UAMH 1497 strain showing the lowest nucleotide sequence similarity and the greatest difference in the morphological and cultural characteristics was set as the outgroup, and a rooted tree was constructed using the *Sporendonema purpurascens* sequence. In the analysis, a total of 604 nucleotides were used as characters. Among them, 394 nucleotides were always constant, and 183 nucleotides showed severe variation, and thus these nucleotides could not be used in the analysis. 31 nucleotides were used in the analysis (parsimony informative characters). The addition of nucleotides was randomly performed, and 100 replications were conducted. As a result, one MP tree was obtained (FIG. 3). It was shown that the tree length was 277, and CI=0.935, RI=0.419, RC=0.392, and HI=0.065. As shown in FIG. 3, the novel *Xylogone ganondermophthora* H55 strain showed a significant difference in the degree of nucleotide substitution from species known to be similar thereto, suggesting that the H55 strain completely differs from these species. Also, bootstrap analysis (heuristic search, 100 replications and a confidence level set at 50) was performed, and only bootstrap support values of 50% or more were indicated on the branches of the tree. As a result, three fungal species, including *Xylogone sphaerospora* ATCC34392, *Arthrographis cuboidea* UAMH 676 and *Scytalidum lignicola* KACC 41228, formed one group, but had a significant difference from the *Xylogone ganondermophthora* H55. Also, the *Sporendonema purpurascens* UAMH 1497 strain which showed a significant difference in the morphological and cultural characteristics shows a significant difference in the degree of nucleotide substitution from the *Xylogone ganondermophthora* H55 strain, and the relationship therebetween was not supported in the bootstrap analysis. Thus, the molecular phylogenic analysis using the nucleotide sequence of the ITS region could confirm that the *Xylogone ganondermophthora* H55 strain is a species completely different from these species.

(4) Analysis of Nucleotide Sequences of RPB2 Gene and 18S rDNA

A fungus similar to the GenBank database using BLASTN was not present. Thus, to determine the accurate molecular systematic position of the H55 strain, the nucleotide sequence of RPB2 gene (gene coding for RNA Polymerase Second largest subunit) was determined by a method similar to the above method. Also, the nucleotide sequence of 18S rDNA (SSU rDNA) was determined by a similar method. The nucleotide sequence of the RPB2 gene of the *Xylogone ganondermophthora* H55 strain is set forth in SEQ ID NO: 4. Also, the nucleotide sequence of the 18S rDNA gene of the *Xylogone ganodermophthora* H55 strain is set forth in SEQ ID NO: 5.

Figure 4:
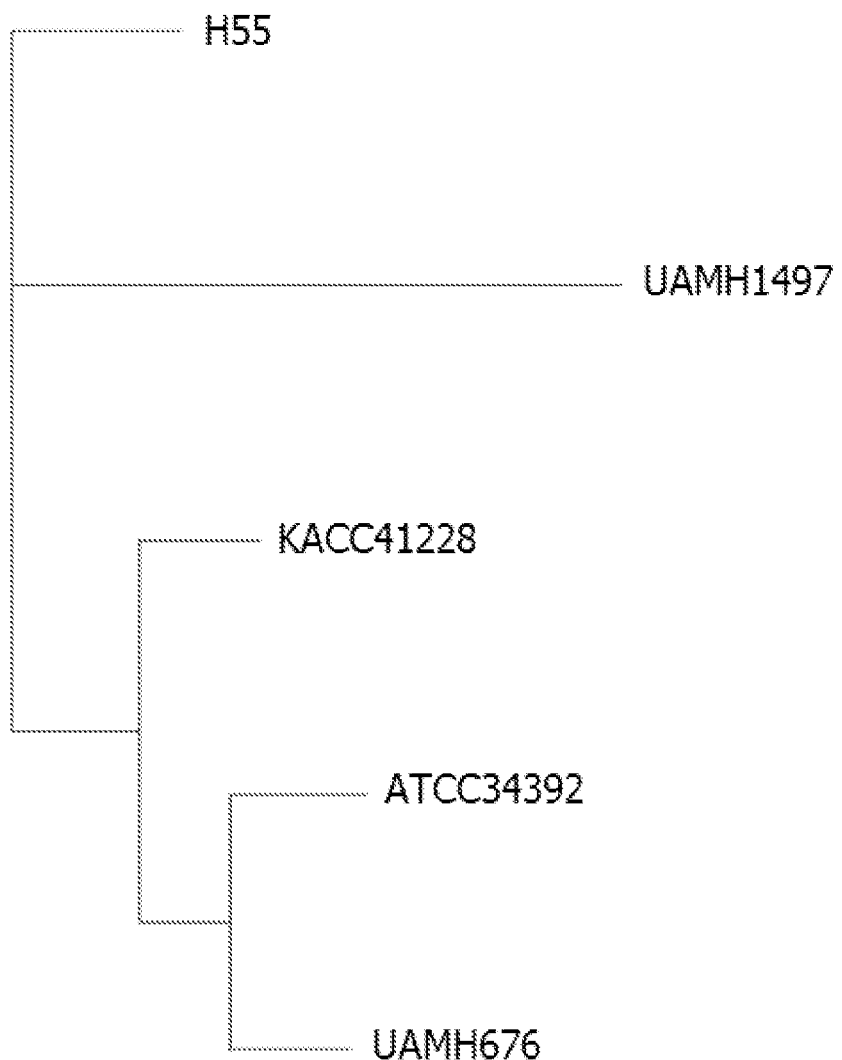

The nucleotide sequence of the RPB2 gene was automatically aligned by the method of Clustal W using the Meg Alignment program, and then the most parsimonious tree (MP tree) was obtained using the PAUP 4.0 beta version statistical program. The optimality criterion was set to maximum parsimony. The nucleotide sequence of a *Sporendonema purpurascens* UAMH 1497 strain showing the lowest nucleotide sequence similarity and the greatest difference in the morphological and cultural characteristics was set as the outgroup, and a rooted tree was constructed using the *Sporendonema purpurascens* sequence. In the analysis, a total of 2222 nucleotides were used as characters. Among them, 1461 nucleotides were always constant, and 562 bases showed severe variation, and thus these nucleotides could not be used. 199 nucleotides were used in the analysis. The addition of nucleotides was randomly performed, and 100 replications were conducted. As a result, one MP tree was obtained. It was shown that the tree length was 1061, and CI=0.870, RI=0.307, RC=0.267, and HI=0.130. As can be seen in FIG. 4, the novel *Xylogone ganondermophthora* H55 strain showed a significant difference in the degree of nucleotide substitution from species known to be similar thereto, suggesting that the H55 strain completely differs from these species.

Also, bootstrap analysis (heuristic search, 100 replications and a confidence level set at 50) was performed, and only bootstrap support values of 50% or more were indicated on the branches of the tree. As a result, there was no group having a bootstrap support value of 50 or more, and thus it could be seen that the fungal species reported to be similar to *Xylogone ganondermophthora* were molecular phylogenetically very different from *Xylogone ganondermophthora*. Accordingly, the molecular phylogenic analysis using the nucleotide sequence of the RPB2 gene could confirm that the *Xylogone ganondermophthora* H55 strain is a species completely different from these species.

Meanwhile, in order to examine the genetic diversity of groups constituting the novel species, 60 strains collected from all parts of Korea were examined using an AFLP (Amplified Fragment Length Polymorphism) method. As a result, it was found that the groups were uniform in about 300 genetic loci, suggesting that the ascomycetous groups constituting the novel species are genetically very uniform.

EXAMPLE 2

Antifungal Activity of Xylogone ganodermophthora Extract Against Phytophthora capsici In order to measure the antifungal activity of an extract of the cultured H55 strain against *Phytophthora capsici*, the following test was carried out.

Figure 5:
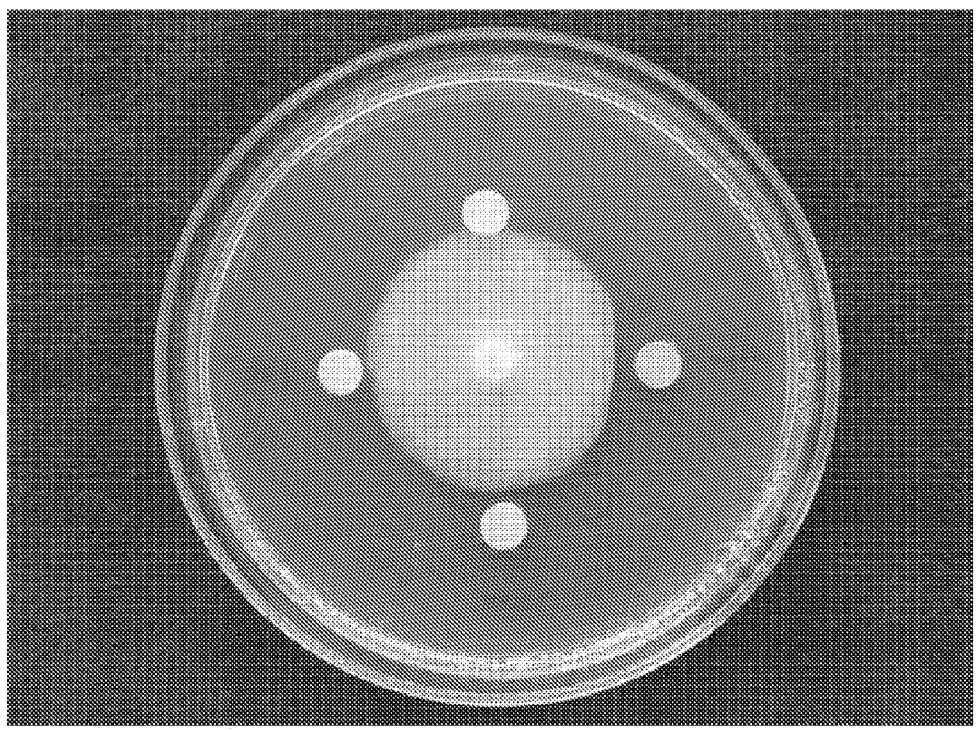
Figure 6:
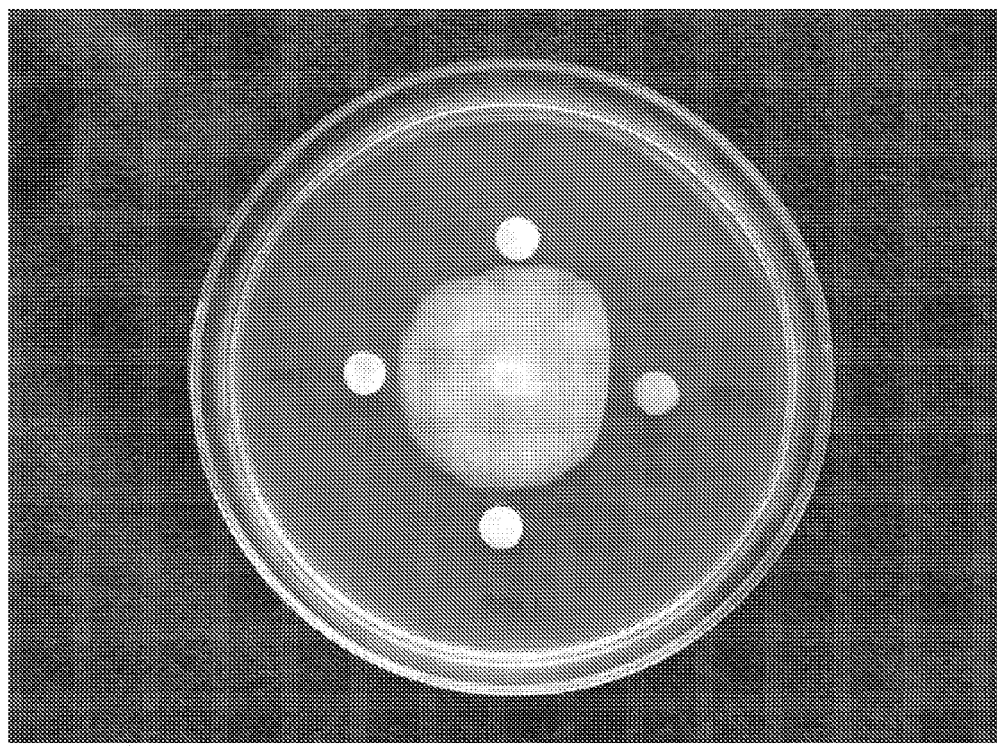

First, the H55 strain stored at −70° C. in Example 1 was inoculated on PDA medium and cultured for 7 days, and the cultured mycelium was inoculated on oak sawdust medium. Among 145 isolated strains, one strain (H55) was inoculated on oak sawdust medium, cultured at 26° C. for 4 weeks, and then extracted with methanol, and the extract was concentrated under reduced pressure. The concentrate was dissolved again in methanol to concentrations of 0, 100, 1,000 and 10,000 ppm, and paper discs were dipped therein. Then, the paper discs were placed at constant intervals a potato dextrose agar medium inoculated with *Phytophthora capsici*, and the degree of inhibition of mycelial growth was examined. When the extract of the H55 strain was cultured for about 3 days, it showed an inhibitory effect on the growth of the *Phytophthora capsici* mycelia at a concentration of 100 ppm or higher (FIG. 5). In addition, the methanol extract was dissolved in methanol, extracted with ethyl acetate, and then concentrated under reduced pressure, and the concentrate was dissolved and tested by the above-described method. As a result, the extract of the H55 strain showed an inhibitory effect on the growth of the *Phytophthora capsici* mycelia at a concentration of 100 ppm or higher (FIG. 6).

Measurement of MIC in Methanol Extract

The methanol extract was dissolved in methanol, and then added to each well of a 24-well cell culture plate. As a control, 1 ml of 1% methanol-containing potato dextrose agar (PDA) medium was used. Meanwhile, the methanol extract was added to 1 ml of medium to final concentrations of 10, 50, 100 and 250 ppm, and then the media were solidified in a clean bench. *Phytophthora capsici* cultured on potato dextrose agar medium was cut with a cork borer (diameter: 4 mm) and placed on the center of the medium treated with the methanol extract, after which it was cultured at 26° C. for 3 days while the growth of the mycelia was measured. As a result, it was shown that the MIC was 50 ppm (Table 1).

TABLE 1

Growth of mycelia on PDA as a function of concentration of methanol extract

| Control | 10 (ppm) | 50 (ppm) | 100 (ppm) | 250 (ppm) |
|---|---|---|---|---|
| 6 mm | 6 mm | 3.2 mm | 1.6 mm | 1.9 mm |

Measurement of MIC in Ethylacetate Extract

The methanol extract was concentrated under reduced pressure, dissolved again in methanol, and then extracted with ethylacetate. The ethylacetate extract was concentrated under reduced pressure, dissolved in ethylacetate, and then added to each well of a 24-well cell culture plate. As a control, 1 ml of 1% ethylacetate-containing potato dextrose agar (PDA) medium was used. Meanwhile, the ethylacetate extract was added to 1 ml of medium to final concentrations of 10, 50, 100 and 250 ppm, and then the media were solidified in a clean bench. *Phytophthora capsici* cultured on potato dextrose agar medium was cut with a cork borer (diameter: 4 mm) and placed on the center of the medium treated with the ethylacetate extract, after which it was cultured at 26° C. for 3 days while the growth of the mycelia was measured. As a result, it was shown that the MIC was 10 ppm (Table 2).

TABLE 1

Growth of mycelia on PDA as a function of concentration of ethylacetate extract

| Control | 10 (ppm) | 50 (ppm) | 100 (ppm) | 250 (ppm) |
|---|---|---|---|---|
| 4.5 mm | 1.3 mm | 0.8 mm | 0.5 mm | 0.2 mm |

Additionally, strains other than the H55 strain were tested for antifungal activity against *Phytophthora capsici*. As a result, it was found that organic solvent extracts of the other cultured strains have antifungal activity against *Phytophthora capsici*.

EXAMPLE 3

Control Effect of Xylogone ganodermophthora Extract for Cucurbitaceous Crops

In order to measure the control effects of the extract of the cultured H55 strain for cucurbitaceous crops, the following test was performed.

The control effects of the extract of the cultured H55 strain prepared in Example 1 were measured. 500 ppm or 1,000 ppm of the extract was sufficiently sprayed onto the leaves of various cucurbitaceous crops infected with *Sphaerotheca fusca*. The extract was sprayed once at the initial stage of the development of *Sphaerotheca fusca*, and at 7 days after the spray of the extract, the control effect of the extract for each crop was measured.

As a result, the extract showed control effects for all the cucurbitaceous crops, and among these effects, the control effect for cucumbers was most excellent (Table 3).

TABLE 3

Control effect for each crop

| Test crops | Treatment | Concentration | Diseased leaf area (%) | Control value |
|---|---|---|---|---|
| Cucumbers | Untreated | | 60 | |
| | Triflumizole | 4,000 fold dilution | 10 | 83.3 |
| | 500 ppm extract | 500 ppm | 20 | 66.7 |
| | 1000 ppm extract | 1000 ppm | 15 | 75.0 |
| Pumpkins | Untreated | | 80 | |
| | Triflumizole | 4,000 fold dilution | 30 | 62.5 |
| | 500 ppm extract | 500 ppm | 35 | 56.3 |
| | 1000 ppm extract | 1000 ppm | 40 | 50.0 |
| Oriental melons | Untreated | | 50 | |
| | Triflumizole | 4,000 fold dilution | 10 | 80.0 |
| | 500 ppm extract | 500 ppm | 30 | 40.0 |
| | 1000 ppm extract | 1000 ppm | 30 | 40.0 |
| Melons | Untreated | | 70 | |
| | Triflumizole | 4,000 fold dilution | 40 | 42.9 |
| | 500 ppm extract | 500 ppm | 50 | 28.6 |
| | 1000 ppm extract | 1000 ppm | 60 | 14.3 |

EXAMPLE 4

Antifungal Activities Xylogone ganodermophthora Extract Against Various Plant Pathogenic Fungi Sterilized PDA was dispensed in a disposable Petri dish, and a solution of the methanol extract in methanol was added thereto at various concentrations and then solidified in a clean bench before use in the test. Fragments of vigorously growing mycelia were inoculated on the prepared medium, and then cultured at 25° C. for 5-15 days while the growth of the mycelia was measured. As a control, 1% methanol-containing potato dextrose agar (PDA) medium was prepared and inoculated with mycelial fragments. The results of examination of MIC are shown in Tables 4 to 10.

TABLE 4

Antifungal activities of *Xylogone ganodermophthora* extract against plant pathogenic fungi on PDA

| Plant pathogenic fungi (scientific names) | MIC (ppm) |
|---|---|
| *Colletotrichum acutatum* | 1,000 |
| *Rhizoctonia solani* | 500 |
| *Fusarium moniliforme* | 250 |
| *Sclerotinia cepivorum* | 500 |
| *Sclerotinia sclerotiorum* | 1,000 |
| *Didymetta bryoniae* | 500 |

TABLE 5

Mycelial growth of *Colletotrichum acutatum* on PDA as a function of concentration of *Xylogone ganodermophthora* extract (mycelial growth measured at 5 days after inoculation)

| | Extract concentration (ppm) | | | | |
|---|---|---|---|---|---|
| | 0 | 100 | 200 | 500 | 1000 |
| Mycelial growth (mm) | 22 | 23 | 22 | 21 | 17 |

TABLE 6

Mycelial growth of *Rhizoctonia solani* on PDA as a function of concentration of *Xylogone ganodermophthora* extract (mycelial growth measured at 5 days after inoculation)

| | Extract concentration (ppm) | | | | |
|---|---|---|---|---|---|
| | 0 | 100 | 200 | 500 | 1000 |
| Mycelial growth (mm) | 42 | 42 | 42 | 40 | 38 |

TABLE 7

Mycelial growth of *Fusarium moniliforme* on PDA as a function of concentration of *Xylogone ganodermophthora* extract (mycelial growth measured at 5 days after inoculation)

| | Extract concentration (ppm) | | | | |
|---|---|---|---|---|---|
| | 0 | 200 | 250 | 500 | 1000 |
| Mycelial growth (mm) | 25 | 25 | 22 | 22 | 20 |

TABLE 8

Mycelial growth of *Sclerotinia cepivorum* on PDA as a function of concentration of *Xylogone ganodermophthora* extract (mycelial growth measured at 5 days after inoculation)

| | Extract concentration (ppm) | | | | |
|---|---|---|---|---|---|
| | 0 | 100 | 200 | 500 | 1000 |
| Mycelial growth (mm) | 21 | 22 | 22 | 18 | 18 |

TABLE 9

Mycelial growth of *Sclerotinia sclerotiorum* on PDA as a function of concentration of *Xylogone ganodermophthora* extract (mycelial growth measured at 5 days after inoculation)

| | Extract concentration (ppm) | | | | |
|---|---|---|---|---|---|
| | 0 | 100 | 200 | 500 | 1000 |
| Mycelial growth (mm) | 44 | 44 | 44 | 44 | 40 |

TABLE 10

Mycelial growth of *Sclerotinia sclerotiorum* on PDA as a function of concentration of *Xylogone ganodermophthora* extract (mycelial growth measured at 5 days after inoculation)

| | Extract concentration (ppm) | | | | |
|---|---|---|---|---|---|
| | 0 | 100 | 200 | 500 | 1000 |
| Mycelial growth (mm) | 20 | 20 | 20 | 18 | 17 |

As described above, a strain according to the present invention or a culture or extract of the strain has antifungal activity against plant pathogenic fungi, including *Phytophthora capsici*. Thus, a formulation for controlling plant diseases, which comprises the above material as an active ingredient, is very useful in the agricultural industry as an environment-friendly strong antifungal agent.

What is claimed is:

1. A method for controlling a plant disease, the method comprising
spraying onto a host plant infected with a plant disease caused by a plant pathogenic fungus a composition comprising an effective amount of an extract obtained from an isolated culture of *Xylogone ganodermophthora* H55, wherein said composition is prepared by:
obtaining an isolated culture of *Xylogone ganodermophthora* H55; and
dissolving the cultured *Xylogone ganodermophthora* H55 in a solvent to obtain said extract, wherein the solvent is selected from the group consisting of water, a $C_{1-4}$ anhydrous or hydrated lower alcohol, ethyl acetate, chloroform, 1,3-butylene glycol, hexane, diethyl ether, and combinations thereof.

2. The method of claim 1, wherein the plant pathogenic fungus is *Phytophthora capsici, Sphaerotheca fusca, Colletotrichum acutatum, Rhizoctonia solani, Fusarium moniliforme, Sclerotinia cepivorum, Sclerotinia sclerotiorum* or *Didymella bryoniae*.

3. The method of claim 2, wherein the plant pathogenic fungus is *Phytophthora capsici* or *Sphaerotheca fusca*.

4. The method of claim 1, wherein the host plant is a *Cucurbitaceae* plant.

5. The method of claim 4, wherein the *Cucurbitaceae* plant is a *Lagenaria, Luffa, Cucurbita* or *Cucumis* plant.

6. The method of claim 5, wherein the *Cucurbitaceae* plant is a gourd, a cucumber, a pumpkin, an oriental melon or a melon.

7. The method of claim 1, wherein the solvent is methanol.

8. The method of claim 1, further comprising, after dissolving, concentrating the extract under reduced pressure, wherein the solvent used for the dissolving is methanol or ethyl acetate.

* * * * *